United States Patent
Baeuerle et al.

[11] Patent Number: 6,148,680
[45] Date of Patent: Nov. 21, 2000

[54] SAMPLE INJECTOR FOR A HIGH-PRESSURE LIQUID CHROMATOGRAPH

[75] Inventors: Martin Baeuerle, Buehlertal; Peter Stemer, Waldbronn, both of Germany

[73] Assignee: Hewlett-Packard Company, Fort Collins, Colo.

[21] Appl. No.: 09/310,734

[22] Filed: May 12, 1999

[30] Foreign Application Priority Data

May 25, 1998 [EP] European Pat. Off. .............. 98109432

[51] Int. Cl.[7] ..................................................... G01N 1/00
[52] U.S. Cl. ......................................................... 73/864.25
[58] Field of Search ........................... 73/864.21–864.25, 73/864.81, 864.85, 864.87, 61.55, 61.56

[56] References Cited

U.S. PATENT DOCUMENTS

| | | |
|---|---|---|
| 4,974,458 | 12/1990 | Koike . |
| 5,264,182 | 11/1993 | Sakagami .............................. 73/864.21 |
| 5,650,846 | 7/1997 | Yin et al. . |
| 5,879,944 | 3/1999 | Komatsu .............................. 73/864.24 |

FOREIGN PATENT DOCUMENTS

0327658 A1  2/1988  European Pat. Off. . 
19616824A1  4/1996  Germany .

*Primary Examiner*—Robert Raevis

[57] ABSTRACT

A sample injector for a high-pressure liquid chromatography system that has an injector needle, which is freely movable within a three dimensional sample space. The needle is attached to a means of transport, which moves in the Y-, Y- and Z-axes. The needle can be moved to various sample intake positions on a sample tray and to the injection position where the sample is injected into the capillary system. The means of transport comprises a mechanism called X-carriage, which is movable in horizontal direction. The X-carriage has jib attached that performs the vertical movement. The jib a robot arm, which can rotate for ±180° in a horizontal plane. The injection needle is attached to the end of the robot arm. The needle is connected with a metering means, through a flexible connection capillary comprising a glass capillary and a plastic coating. The combination of known high-pressure injection systems with a flexible capillary has the advantage that even the most minute sample can be injected in the analysis cycle without losses.

6 Claims, 3 Drawing Sheets

SAMPLE INJECTOR FOR A HIGH-PRESSURE LIQUID CHROMATOGRAPH

FIELD OF THE INVENTION

The invention relates to a sample injector for high-pressure liquid chromatographs. Such injectors are used to inject a sample. which is to be chromatographically analysed, into the chromatographic column.

BACKGROUND OF THE INVENTION

From EP 0 327 658 A1, a high-pressure sample injector for a liquid chromatograph is known with which samples can be injected by using metering means and a capillary system with a generally known six-port valve for the individual process steps. In the known sample injector, the needle is raised in order to place a sample container for sample intake underneath the needle.

Subsequently, after removal of the sample container, the defined sample quantity taken up is injected into a seat in order to inject the sample quantity into the chromatography system. Metering means being capable for high-pressure sample injection which is permanently rinsed has the advantage that no loss of sample material occurs, when compared to metering devices not being capable for high-pressure. However, the known sample injector has the disadvantage that the sample must be transported to the needle and consequently, often much more sample material must be provided than is actually used.

It is thus an object of the present invention to propose a high-pressure sample injector which has the needle freely movable in a three-dimensional sample area with a metering device being capable for high-pressure injection and connected to the high-pressure liquid path.

SUMMARY OF THE INVENTION

According to the invention, a the sample injector comprises a needle which is movable along the X, Y and Z axes to the various sample intake positions on a sample tray and to an injection position where the sample is injected into the capillary system. To move the needle within the three-dimensional sample space, the means of transport comprises a mechanism called X-carriage, which is movable in horizontal direction. The X-carriage has a jib attached that performs the vertical movement. The jib holds a robot arm, which can rotate for ±180° in a horizontal plane. The injection needle is attached to the end of the robot arm. In addition, for the free movement of the needle in all directions in a sample area, the needle is connected to a flexible connection capillary, made from a glass capillary and a plastic coating. Due to the invention, the samples can now also be provided in so-called well plates in which a multitude of small indentations arranged side by side are provided to take up the sample liquid. Due to the hinging range of twice 180°, the flexible connection capillary bends in both directions, however without kinking and without stopping the transport of liquid. For this purpose, a connection capillary can be used as it is described for example in EP 0 698 789 A1for connection to a detector cell within a chromatography system.

Thus with the sample injector according to the invention it is possible to maintain the advantages of the injection mode described in EP 0 327 658 B1and at the same time to move the needle to the sample, whereby the connection capillary on the one hand allows a pressure up to 400 bar while at the same time maintaining frequent bending cycles.

According to a particular embodiment, the connection capillary is guided within the robot arm which in turn is held with the jib on a supporting frame which makes possible vertical movement and X-slide movement of the jib. In this context, X-slide movement means that, while a given position in X-Y-coordinates is transferred in polar coordinates comprising a X-direction and an angle, the jib makes movements in the X axis while the rotation angle to reach the sample is carried out by the rotation arm. In the area of this supporting frame, the moveable glass capillary is at least partially kept within bent tubular guides and outside the supporting frame the said capillary is connected to the metering means by way of a high-pressure resistant fitting. Thus the flexible connection capillary can be threaded through the guide up to the needle and fitted to the needle and can be connected at the other end to the metering means.

According to a further preferred embodiment, the flexible connection capillary is made from a quartz glass and a PEEK casing and has a pressure stability of at least 400 bar, whereby for a range of up to 0.6 mm exterior diameter of the quartz capillary, the diameter ratio of exterior diameter to interior diameter is at least 2.4. These special characteristics ensure the strength of the connection capillary in regard to the pressure while at the same time providing mobility. In order to also ensure that a minimal bending radius is maintained, the ratio of exterior diameter to minimum bending radius in the area of the robot arm is at least 0.018.

BRIEF DESCRIPTION OF THE DRAWINGS

Below, the invention is explained in more detail by means of one embodiment in accord with the following figures.

DETAILED DESCRIPTION OF THE INVENTION

Figure 1:
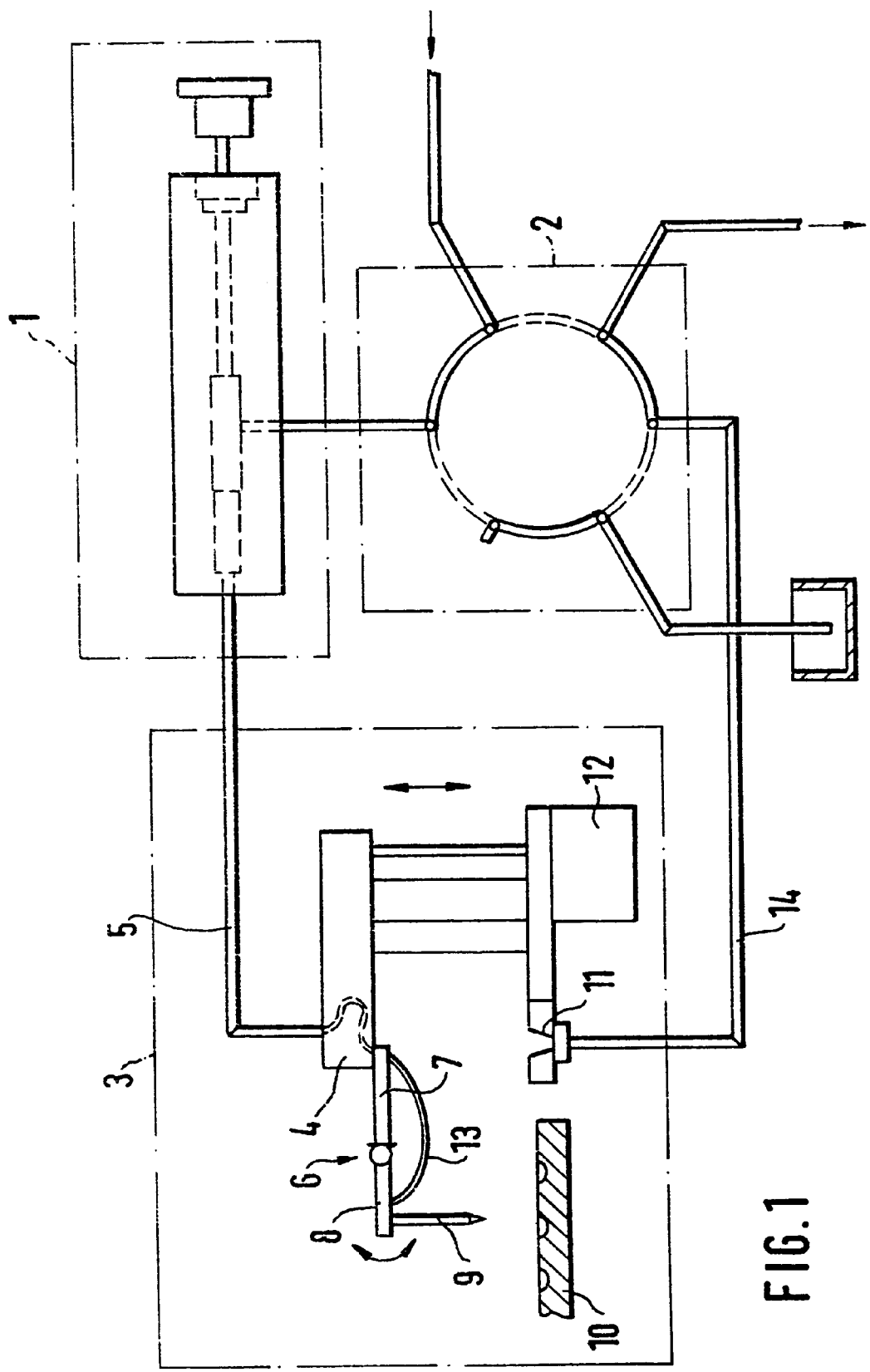
FIG. 1 shows an embodiment of a sample injector with a metering means, a capillary system as well as a means for moving the needle.

FIG. 1 shows the basic functions of the individual elements of the sample injector and their connections.

Shown are the metering means 1, the distributor system 2 with the capillary system and the means 3 for taking in the sample and injecting it into the capillary system which means 3 is connected both with the metering means and with the distributor system. The way the distributor means 2 as well as the metering means 1 function is for example explained in EP 327 658 A1. The means 3 comprises a mounting 4 which is movable in vertical direction and connected to the metering means 1 by way of a conduit 5. On the mounting 4 there is a robot arm 6 comprising a jib 7 and a rotation arm 8 coupled to the free end. Attached to the free end of the rotation arm 8 is the needle 9 for receiving the sample liquid from sample containers 10 and injecting it into the seat 11 in the receptacle 12. The arm 8 is hingeable by ±180° in relation to the arm 7 and as a result, the needle 9 is connected to the conduit 5 by a flexible connection capillary 13. The sample intake 10 comprises a tray with individual indentations for the sample liquid. The seat 11 is connected to the distributor means 2 via the conduit 14.

Figure 2:
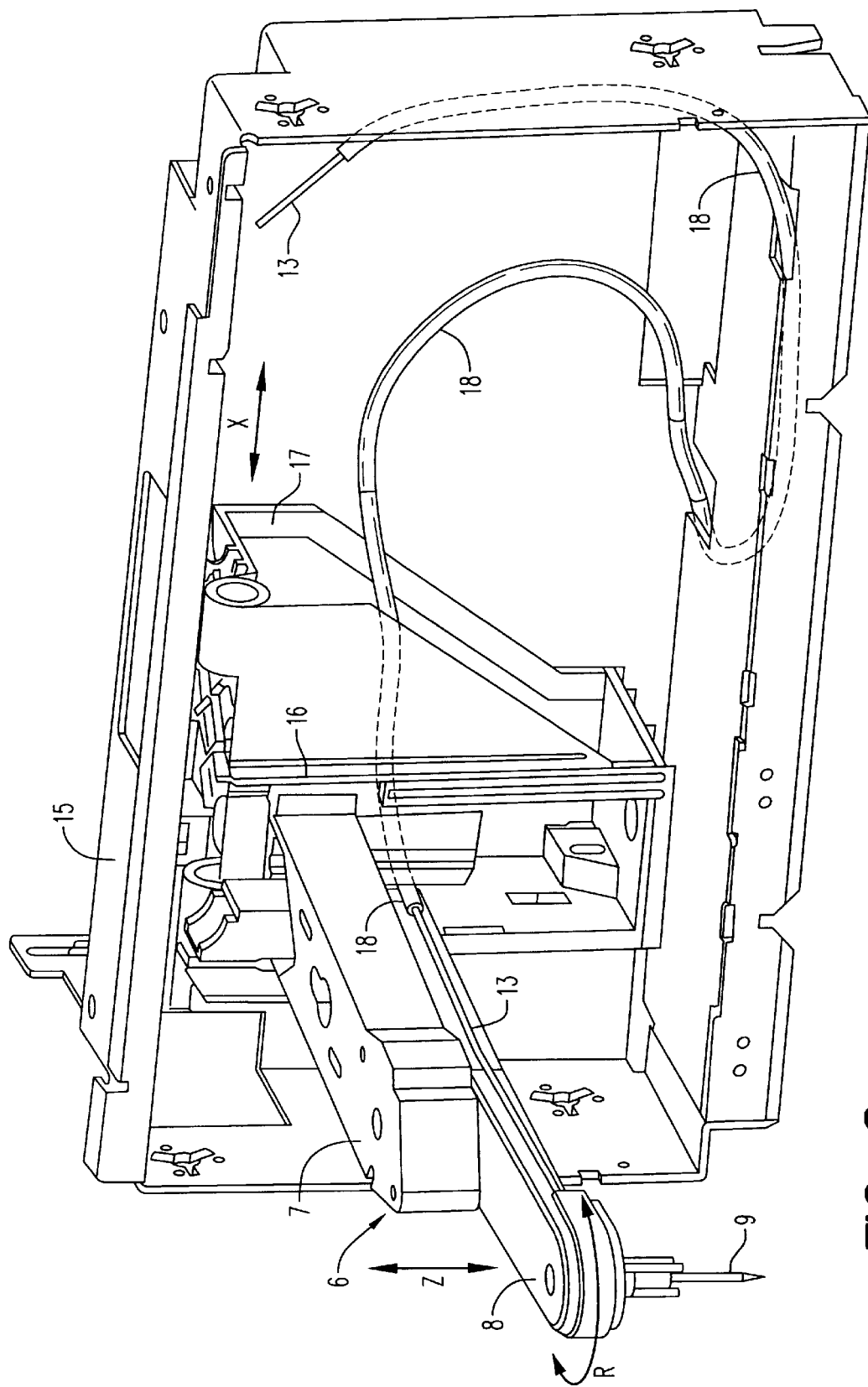
FIG. 2 is a perspective view of the means for moving the needle with the mechanism for the XYZ movement and the sample trays.

FIG. 2 shows an exemplary embodiment with a supporting frame to which the robot arm 6 is attached. A mechanism 16 for vertical movement of the robot arm 6 as well as a mechanism 17 for the sliding movement of arm 7 is provided on the supporting frame. FIG. 2 also shows the sample needle arranged at the free end of arm 8. In this drawing, the flexible connection capillary 13 is routed from the point where the needle 9 is attached to the arm 8, in the robot arm 6 to the supporting frame 15 and is guided in the supporting frame 15 in tubular guides 18 so that the flexible connection capillary can follow the movements of the robot arm 6 in relation to the supporting frame 15 as well. The tubular guides are partly bent to provide the connection capillary with a clear guide and curvature. The connection capillary 13 is threaded into the individual guides and connected to the needle 9 by means of a respective fitting. At the other end there is a respective connection (not shown) to the metering means 1, for example by way of conduit 5 of FIG. 1.

In one embodiment, the glass capillary measures approx. 1.10 m and has an exterior diameter of 350 to 600 $\mu$m.

The glass capillary comprises quartz glass or borosilicate glass and the coating comprises polyetheretherketone (PEEK). The combination of quartz glass and plastic coating provides pressure stability, in particular with a diameter ratio of exterior diameter to interior diameter of at least 2.4 at an exterior diameter of the glass capillary of up to 600 $\mu$m. The connection capillary is 0.8 to 1.6 mm in diameter to ensure the necessary resistance to pressure.

Figure 3:
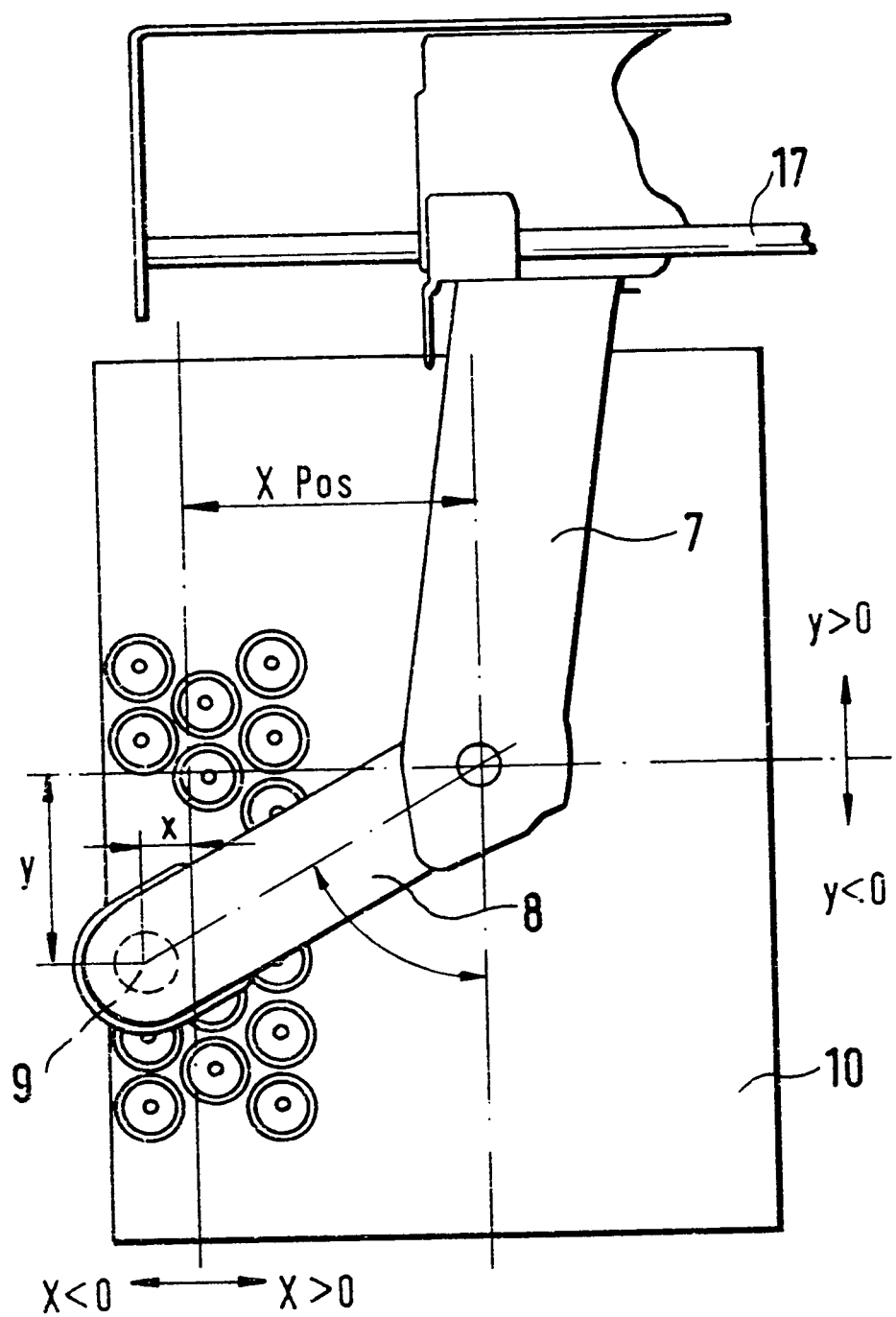
FIG. 3 shows the principal movement of the robot arm in the X and Y axes.

FIG. 3 shows the basic movements of the robot arm 6 with X-slide movement of the jib 7 as well as the movement of the needle 9 at the free end of the robot arm 2 in X and Y axes by moving the rotation arm 8 at an angle and a respective sample tray 10 with recesses (well plate).

What is claimed is:

1. A sample injector for a high-pressure liquid chromatograph, comprising:
    a sample needle through which a sample which is to be chromatographically analyzed can be drawn in by action of a metering device;
    a means for moving the needle into a sample intake position and into a sample injection position;
    a capillary system for transporting solvent delivered by a solvent delivery system at high pressure to a chromatographic column and for transferring samples to the chromatographic column;
    said metering device being adapted for drawing a metered amount of sample through the sample needle and for releasing this amount of sample when the metering means is connected to the solvent delivery system, characterized in that
    by the means for moving the needle in X, Y, Z axes, the sample needle is movable to various sample intake positions on a sample tray and to the injection position in which position injection into the capillary system takes place, whereby the means comprises a mechanism for vertical movement and a robot arm comprising a jib for X-slide movement and a rotation arm which is freely hingeable at the free end of the jib and which is in a position to carry out movements ±180° in order to position the sample needle attached to the free end of the rotation arm along the X and Y axes;
    and in that the sample needle for high-pressure injection is connected to a flexible connection capillary comprising a glass capillary and a plastic coating.

2. A sample injector according to claim 1, wherein the flexible connection capillary is retained in a supporting frame in which the jib is movably retained in vertical axis and in the X-axis, is routed at least partly inside curved tubular guides.

3. A sample injector according to claim 2, wherein outside the supporting frame the flexible connection capillary is connected to the metering means by way of a high-pressure resistant fitting.

4. A sample injector according to claim 1, wherein the flexible connection capillary comprises a quartz glass with a polyetheretherketone casing.

5. A sample injector according to claim 4, wherein the flexible connection capillary has a pressure stability of at least 400 bar, and for a range of up to 0.6 mm exterior diameter of the quartz capillary, the diameter ratio of exterior diameter to interior diameter is at least 2.4.

6. A sample injector according to claim 4, wherein the ratio of exterior diameter to minimum bending radius in the area of the arms is at least 0.018.

* * * * *